(12) United States Patent
Castelijns

(10) Patent No.: US 9,328,052 B2
(45) Date of Patent: May 3, 2016

(54) PROCESS TO PRODUCE ALKENOIC ACID ESTERS FROM LACTONES

(71) Applicant: Anna Maria Cornelia Francisca Castelijns, Echt (NL)

(72) Inventor: Anna Maria Cornelia Francisca Castelijns, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 556 days.

(21) Appl. No.: 13/722,241

(22) Filed: Dec. 20, 2012

(65) Prior Publication Data

US 2013/0158286 A1 Jun. 20, 2013

Related U.S. Application Data

(60) Provisional application No. 61/578,068, filed on Dec. 20, 2011.

(30) Foreign Application Priority Data

Dec. 20, 2011 (EP) .................................... 11194500

(51) Int. Cl.

| | | |
|---|---|---|
| C07C 67/38 | (2006.01) | |
| C07C 67/30 | (2006.01) | |
| C07C 67/03 | (2006.01) | |
| C07C 67/36 | (2006.01) | |
| C07C 51/09 | (2006.01) | |
| B01J 38/60 | (2006.01) | |
| B01J 38/62 | (2006.01) | |
| B01J 29/90 | (2006.01) | |
| B01J 21/20 | (2006.01) | |
| B01J 21/12 | (2006.01) | |
| B01J 29/70 | (2006.01) | |

(52) U.S. Cl.
CPC ................. *C07C 67/03* (2013.01); *B01J 21/20* (2013.01); *B01J 29/90* (2013.01); *B01J 38/60* (2013.01); *B01J 38/62* (2013.01); *C07C 51/09* (2013.01); *C07C 67/36* (2013.01); *C07C 67/38* (2013.01); *B01J 21/12* (2013.01); *B01J 29/7007* (2013.01); *B01J 2229/37* (2013.01)

(58) Field of Classification Search
CPC ................................ C07C 67/38; C07C 67/03
See application file for complete search history.

(56) References Cited

U.S. PATENT DOCUMENTS

| | | | | |
|---|---|---|---|---|
| 2,206,311 | A | * 7/1940 | Thompson | .................... 562/515 |
| 2,368,366 | A | * 1/1945 | Kyrides et al. | ................ 549/326 |
| 3,684,738 | A |   8/1972 | Chen et al. | |
| 4,740,613 | A | * 4/1988 | Fischer et al. | ................ 560/205 |
| 4,788,326 | A |  11/1988 | Hoelderich et al. | |
| 4,826,792 | A |   5/1989 | Le et al. | |
| 4,861,912 | A | * 8/1989 | Drent et al. | ................... 560/204 |
| 5,144,061 | A | * 9/1992 | Hoelderich et al. | ......... 560/212 |

FOREIGN PATENT DOCUMENTS

EP          0 499 248 A1     8/1992

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Solomons, Organic Chemistry, 5th Edition, 1992, John Wiley & Sons, Inc., New York, pp. 778-780.*
European Search Report of EP 11 19 4500, Dated Feb. 27, 2012.
Carine E. Chan-Thaw et al., "New generation biofuels: γ-valerolactone into valeric esters in one pot†‡." RSC Advances, vol. 3 (2013), 1302-1306.

* cited by examiner

*Primary Examiner* — Paul A Zucker
(74) *Attorney, Agent, or Firm* — Miles & Stockbridge PC

(57) ABSTRACT

This invention relates to a process for the preparation of alkenoic acid esters comprising contacting a lactone with an alcohol and an acidic heterogeneous catalyst, characterized in that the process is carried out in the presence of at least 20 ppm of an acid having a pKa of 5 or less, relative to the amount of the lactone. The presence of at least 20 ppm of an acid having a pKa of 5 or less may stabilize the catalyst during the reaction and may also be used for reactivating an acidic heterogeneous catalyst. The improved yield advantageously allows energy conservation.

13 Claims, No Drawings

PROCESS TO PRODUCE ALKENOIC ACID ESTERS FROM LACTONES

CROSS REFERENCE TO RELATED APPLICATIONS

This application claims priority to European Application No. 11194500.2 filed Dec. 20, 2011, and Provisional Application No. 61/578,068 filed Dec. 20, 2011, the contents of which are both incorporated herein by reference in their entireties.

BACKGROUND

1. Field of the Invention

The present invention relates to a process for the production of alkenoic acid esters from lactones.

2. Description of Related Art

The present invention relates to a process for the preparation of alkenoic acid esters comprising contacting a lactone with an alcohol and an acidic heterogeneous catalyst. Such a process is known in the art and is described e.g. in U.S. Pat. No. 5,144,061 and U.S. Pat. No. 4,740,613.

The inventors have found that a problem of the processes as described in e.g. U.S. Pat. No. 5,144,061 and U.S. Pat. No. 4,740,613 is that the acidic catalysts tend to deactivate in time. This forms a problem since the conversion or turnover number (TON) and/or the selectivity decreases resulting in higher production cost due to slower processes and because the catalyst needs to be replenished or replaced more frequently.

It is therefore an aim of the invention to provide a process for the preparation of alkenoic acid esters comprising contacting a lactone with an alcohol which results in a higher TON and/or better selectivity. It is another aim of the invention to provide a process for the preparation of alkenoic acid esters comprising contacting a lactone with an alcohol and an acidic heterogeneous catalyst, wherein said catalyst does not inactivate or to a lesser extent.

SUMMARY

In a first aspect the invention provides a process for the preparation of alkenoic acid esters comprising: (a) contacting a lactone with an alcohol and an acidic heterogeneous catalyst, characterised in that the process is carried out in the presence of at least 20 ppm of an acid having a pKa of 5 or less, relative to the amount of the lactone.

DETAILED DESCRIPTION OF A PREFERRED EMBODIMENT

The inventors have surprisingly found that using a strong acid, such as having a pKa of 5 or less in the preparation of alkenoic acid esters from lactone using an acidic heterogeneous catalyst may result in stabilisation of said catalyst such that less or preferably no deactivation of said catalyst may occur. The process of the invention has preferably good selectivity and productivity towards the formation of alkenoic acid esters. Preferably said selectivity and yield towards the formation of alkenoic acid esters is equal or even better than those of processes known in the art. The improved yield advantageously allows for energy conservation.

In the context of the invention "the presence of at least 20 ppm of an acid having a pKa of 5 or less, relative to the amount of the lactone" is understood to refer to the initial presence of said acid prior to the start of the reaction, when no or hardly any lactone and/or alkanol has been converted.

The temperature of the process of the invention is typically between 50 and 450° C. Preferably, the temperature is between 150 and 400° C., more preferably between 200 and 350° C., even more preferably between 225 and 300° C., and most preferably between 245 and 280° C. Lower temperatures, for example temperatures of less than 400° C., less than 350° C., less than 300° C., or less than 280° C. are advantageous because the selectivity towards the alkenoic acid esters may be better as compared to using higher temperatures. Higher temperatures, for example temperatures of more than 150° C., more than 200° C., more than 225° C., more than 245° C. are advantageous because the TON may be better as compares to using lower temperatures.

The molar ratio of lactone to alcohol in the process according to the invention typically ranges from 1:0.5 to 1:10, preferably from 1:1 to 5.

The pressure in the process according to the invention typically ranges from 0.1 to 100 bar, preferably from 0.5 to 10 bar.

The weight hourly space velocity through the catalyst is typically maintained in the range from 0.1 to 20 g, preferably from 0.1 to 5 g of lactone per g of catalyst per hour.

The acidic heterogeneous catalyst may comprise a zeolite. Said zeolite may be any suitable zeolitic catalyst. For example, the zeolitic catalyst may be of the ZSM types, for example ZSM-5. Other suitable zeolytic catalysts are e.g. ZSM-5 CBV2314Cy (Zeolyst), Zeolyst ZSM-5 CBV8014CY (Zeolyst).

The acidic heterogeneous catalyst may comprise a beta zeolite. Beta zeolites (or Zeolite beta) are known in the art. Zeolite beta consists of an intergrowth of two distinct structures termed Polymorphs A and B. Both polymorphs grow as two-dimensional sheets and the sheets random alternate between the two. The polymorphs have a three dimensional network of 12-ring pores.

The acidic heterogeneous catalyst may comprise an amorphous silica-alumina catalyst. Suitable amorphous silica-alumina catalysts include Silica-alumina 1D-6D (Albemarle Catalyst Co.).

Any acid having a pKa of 5 or less can be used. In the context of the invention the pKa of an acid may be established by measuring the pKa in an aqueous solution at 18° C. Examples of preferred acids are sulphonic acids, such as for example trifluoromethanesulphonic acid, p-toluenesulphonic acid, 2,4,6-trimethylbenzene sulphonic acid, 2-hydroxypropane-2-sulphonic acid, tert-butyl sulphonic acid, and methyl sulphonic acid. In a preferred embodiment the acid is methanesulphonic acid or p-toluenesulphonic acid. The use of any such acid may be advantageous in that it may not be required to use other, costly stabilisers that may interfere with the reaction components.

The pKa of the acid in the process of the invention is preferably 4.5 or less, more preferably 4 or less, 3.5 or less, even more preferably 3 or less.

The amount of the acid having a pKa of 5 or less is preferably between 20 and 1000 ppm relative to the amount of lactone. The skilled person will understand that the amount of acid may depend in the pKa; stronger acids may require lower amounts whereas weaker acids may require higher amounts.

The process of the invention may comprise the step of adding acid. The acid may be added to the process in any conceivable way. If, for example, after determining the acid content of the reaction components and calculating the theoretical acid content of the process after adding said components, the skilled person finds that the resulting acid content would be too low (i.e. less than 20 ppm) the skilled person may add acid to one or more of said reaction components to an extent that the resulting amount of acid in the process will be at least 20 ppm relative to the amount of the lactone.

In one embodiment the acid is added separately, i.e. the acid is added in addition to the other reaction components. The reaction components and the separately added acid may be added to the process in any order. For example, the acid may be added before adding the reaction components, or adding one of the reaction components but before adding the other reaction components etc., or at the end, or anywhere in-between, as along adding the acid results in the initial presence of at least 20 ppm relative to the amount of the lactone.

Of course, when in the context of the invention it is referred to that the "acid is added separately" this does not necessarily mean that the reaction components do not or must not comprise any acid. If the reaction components do not comprise any acid it follows that the acid should be added separately. If, on the other hand, the reaction components do comprise acid but, after determining the acid content of the reaction components and calculating the theoretical acid content of the process after adding said components, the skilled persons finds that the resulting acid content would be less than 20 ppm, then additional acid may be added separately such that the resulting amount of acid is at least 20 ppm relative to the amount of the lactone.

The acid may also be added after the reaction has started, i.e. when the alkenoic acid ester is already being formed.

The skilled person will understand that the amount of acid can be expressed relative to the amount of initial lactone even when a certain amount of lactone has already been converted. The skilled person simply needs to establish the initial amount of lactone in order to establish the suitable amount of acid to be added.

The acid may also be added at more than one stage, for example: part of the acid may be added before the start of the reaction and part of the acid may be added after the reaction has started.

In an embodiment the process of the invention is carried out in the presence of at least 0.26% water. The amount of water in the process of the first aspect of the invention is preferably at least 0.26% wt, more preferably at least 0.28% wt, at least 0.5% wt, at least 1% wt, even more preferably at least 1.1% wt, at least 1.2% wt, even more preferably at least 2% wt, 2.2% wt, 2.4% wt, at least 2.5% wt, even more preferably at least 4.5% wt, even more preferably at least 5% wt all relative to the amount of the lactone. The amount of water is preferably 10% wt or less, more preferably 8% wt or less, even more preferably 5% wt or less, all relative to the amount of the lactone. The skilled person can readily determine the water content of said reaction components, for example using Karl Fischer titration.

The alcohol is preferably an alkanol, preferably having one, two, or three carbon atoms and is preferably unbranched. Suitable alkanols are methanol, ethanol and propanol. A preferred alkanol is methanol.

The lactone may comprise 5-methylbutyrolactone (also referred to as [gamma] valerolactone).

In an embodiment the alcohol is methanol and the lactone is 5-methylbutyrolactone, thereby forming pentenoic acid methyl ester. Pentenoic acid methyl esters (or methylpentenoates) are important intermediates in the production of adipic acid from renewable sources. Adipic acid itself is an intermediate in the production of 6.6 polyamide (nylon). The most important process to produce adipic acid is based on oil and starts from benzene. In this process benzene is hydrogenated to cyclohexane. Cyclohexane is then oxidised using $HNO_3$ as oxidant to adipic acid. A disadvantage of this process is that it is based on fossil derived oil. Another disadvantage is the evolution of $NO_x$ during the oxidations step, which either is vented to the air, which is highly undesirable as it is a greenhouse gas, or is catalytically destroyed, which is an expensive process. New processes for the production of adipic acid have been developed based on butadiene, which is converted tot methyl 3-pentenoate. The next step is isomerisation of methyl 3-pentenoate to methyl 4-pentenoate which can be converted to dimethyladipate. A disadvantage of the butadiene-based processes is the high cost of butadiene. A second disadvantage is the low rate of the methoxycarbonylation of butadiene. Another process for the production of adipic acid starts from levulinic acid as a renewable source. Levulinic acid may be produced from agricultural waste products or waste from the paper industry or municipal waste and therefore constitutes a renewable source of a C-5 fragment. The hydrogenation of levulinic acid has been described and produces γ-valerolactone in high yield.

The pentenoic acid methyl ester may be an isomeric mixture of pentenoic acid methyl esters.

In an embodiment the process of the invention is a continuous process. The use of the acid having a pKa of 5 or less is particularly advantageous in continuous processes because in such processes the stability of the catalyst is crucial. A continuous process can only be performed satisfactorily if the catalyst can be left in the reactor and when it does not have to be replaced or replenished, or at least as little as possible.

In another embodiment the process of the invention is a repetitive batch process, wherein the process further comprises:

(b) recovering the acidic heterogeneous catalyst from the alkenoic acid esters in the presence of said acid having a pKa of 5 or less, wherein the amount of said acid having a pKa of 5 or less in the recovered acidic heterologous catalyst is at least 20 ppm relative to the amount of lactone; and (c) repeating step (a) wherein at least part of the acidic heterogeneous catalyst in step (a) is the recovered acidic heterologous catalyst obtained in step (b).

In repetitive batch processes the catalyst is recycled between the reaction batches. Inactivation of a catalyst may occur between recovering the catalyst from the reaction product and the start of the subsequent (batch) reaction. In the process of the invention the acidic heterogeneous catalyst may be stabilised by recovering the catalyst in the presence of the acid.

In an embodiment, the 5-methylbutyrolactone is produced by converting levulinic acid to 5-methylbutyrolactone in a hydrogenation reaction. Such processes are for example described in L. E. Manzer, *Appl. Catal. A,* 2004, 272, 249-256; J. P. Lange, J. Z. Vestering and R. J. Haan, *Chem. Commun.,* 2007, 3488-3490; R. A. Bourne, J. G. Stevens, J. Ke and M. Poliakoff, *Chem. Commun.,* 2007, 4632-4634; H. S. Broadbent, G. C. Campbell, W. J. Bartley and J. H. Johnson, *J. Org. Chem.,* 1959, 24, 1847-1854; R. V. Christian, H. D. Brown and R. M. Hixon, *J. Am. Chem. Soc.,* 1947, 69, 1961-1963; L. P. Kyrides and J. K. Craver, U.S. Pat. No. 2,368,366, 1945; H. A. Schuette and R. W. Thomas, *J. Am. Chem. Soc.,* 1930, 52, 3010-3012.

In another embodiment the levulinic acid is prepared by converting a C6 carbohydrate to levulinic acid in an acid-catalysed reaction. Such processes are for example described in L. J. Carlson, U.S. Pat. No. 3,065,263, 1962; B. Girisuta, L. P. B. M. Janssen and H. J. Heeres, *Chem. Eng. Res. Dev.,* 2006, 84, 339-349; B. F. M. Kuster and H. S. Vanderbaan, *Carbohydr. Res.,* 1977, 54, 165-176; S. W. Fitzpatrick, WO8910362, 1989, to Biofine Incorporated; S. W. Fitzpatrick, WO9640609 1996, to Biofine Incorporated. Examples of C6 carbohydrates are glucose, fructose, mannose and galactose. Preferred raw material for the C6 carbohydrates is lignocellulosic material containing carbohydrate based polymers composed partly or entirely from C6 sugars such as cellulose, starch and hemicellulose. The C6 carbohydrate may comprise other components, such as plant waste, paper waste, sewage etc.

In another aspect the invention provides a process to produce adipic acid dimethyl ester comprising converting the pentenoic acid methyl ester produced in the process of the first aspect of the invention to adipic acid dimethyl ester in a carbonylation reaction in the presence of CO and methanol. Such carbonylation processes are well known in the art and are described e.g. in WO2001068583.

In a further aspect the invention provides a process to produce adipic acid comprising converting the adipic acid dimethyl ester produced in the second aspect of the invention in a hydrolysis reaction. The process to produce adipic acid according to the third aspect of the invention advantageously allows the use of renewable sources such as plant waste, sewage waste etcetera's instead of using fossil sources.

In a further aspect the invention provides a process to improve the TON of an acidic heterogeneous catalyst, the process comprising contacting said acidic heterogeneous catalyst with an acid having a pKa of 5. The acidic heterogeneous catalyst is preferably suitable for the preparation of alkenoic acid esters from a lactone in the presence of an alcohol.

In a further aspect the invention provides a process for the reactivation of an (at least partially) inactivated acidic heterogeneous catalyst, the process comprising the step of:
 contacting said acidic heterogeneous catalyst with an acid having a pKa of 5 or less.

A problem of the use of an acidic heterogeneous catalyst in chemical conversion reactions such as the conversion of a lactone and an alcohol to an alkenoic acid ester is that the catalyst may deactivate over time. Consequently, when such acidic heterogeneous catalyst is recovered from the chemical conversion process, it may be observed that its activity has decreased as compared to a "fresh" acidic heterogeneous catalyst, i.e. a catalyst that has not yet been used in the chemical conversion reaction. In other words, the catalyst may be (at least partially) inactivated. Contacting said (at least partially) inactivated, acidic heterogeneous catalyst with an acid having a pKa of 5 or less may (at least partially) restore the TON. Said acidic heterogeneous catalyst is preferably suitable for the preparation of alkenoic acid esters from a lactone in the presence of an alcohol. It will be clear to the skilled person that the (at least partially) inactivated catalyst does not necessarily have to be completely reactivated. Even partial reactivation of the catalyst is already economically very attractive. Therefore, the process for the reactivation of an (at least partially) inactivated acidic heterogeneous catalyst includes partial reactivation, for example reactivation to a TON of at least 50%, preferably at least 60%, at least 70%, more preferably at least 80%, at least 90%, even more preferably at least 95% as compared to the TON of said acidic heterogeneous catalyst which has not yet been used in used in a chemical conversion reaction.

In an embodiment, the (at least partially) inactivated, acidic heterogeneous catalyst is obtainable from a process for said preparation.

In an embodiment, the relative TON of the (at least partially) inactivated, acidic heterogeneous catalyst (i.e. before reactivation) is preferably 90% or less, 80% or less, more preferably 70% or less, 60% or less, even more preferably 50% or less, 40% or less, 30% or less, even more preferably 20% or less, or 10% or less, as compared to the TON of said acidic heterogeneous catalyst which has not yet been used in used in a chemical conversion reaction. Within the context of the process for the reactivation of the (at least partially) inactivated acidic heterogeneous catalyst, the relative TON of the (at least partially) inactivated, acidic heterogeneous catalyst may be established by measuring the TON of the at least partially) inactivated catalyst, i.e. a catalyst which has been used in a certain chemical conversion reaction and comparing this value with the TON of the same acidic heterogeneous catalyst but which catalyst had not yet been used before in this chemical conversion reaction, or, preferably, which catalyst has not been used in any chemical conversion reaction. The skilled person will understand that in order to properly compare the TON of the used (that is, the (at least partially) deactivated) catalyst with the TON of the unused catalyst, the reaction conditions for both catalyst species need to be the same.

In an embodiment, the process for the reactivation of an (at least partially) deactivated acidic heterogeneous catalyst comprises, prior to the step of contacting an acidic heterogeneous catalyst with an acid having a pKa of 5, the step of:
 recovering said (at least partially) inactivated acidic heterogeneous catalyst from a process for the preparation of alkenoic acid esters from a lactone in the presence of an alcohol.

Optionally, the process for the reactivation of an (at least partially) inactivated acidic heterogeneous catalyst comprises, after the step of contacting the acidic heterogeneous catalyst with an acid having a pKa of 5, the step of:
 recovering the (at least partially) reactivated acidic heterogeneous catalyst from the acid.

The invention will be further elucidated with reference to the following examples, without however being limited thereto.

EXAMPLES

Abbreviations

DME, dimethylether
M-2P, methyl-2-pentenoate
M-3P, methyl-2-pentenoate
M-4P, methyl-2-pentenoate
MP, methylpentenoate
VL, valerolacton
PA, pentenoic acid
LHSV, Liquid Hourly Space Velocity (=ml of feed/ml of catalyst hour)
WHSV, Weight Hourly Space Velocity (=grams of feed/gram of catalyst hour)

Materials & Methods

Zeolyst CP 7146, acidic beta zeolitic catalyst, was obtained from Zeolyst International, P.O. Box 830, Valley Forge, Pa. 19482 USA. Silica-alumina 1D and silica-alumina 3D amorphous catalysts were obtained from Albemarle Catalyst Company BV, Nieuwendammerkade 1/3, 1022 AB Amsterdam, the Netherlands. Water content was determined by Karl Fischer titration. Valerolactone and methanol were obtained from Aldrich Co.

Example 1

A tubular reactor (total length, 0.47 m; total volume, 120 mL; having an upper and lower section each having a diameter of 12.7 mm, a length of 4 cm, and a volume of 15 mL; and having an intermediate heated section having a diameter of 20 mm and a volume of 105 mL) was filled with 50 ml of catalyst. A gaseous mixture of methanol, γ-valerolacton and $N_2$ (5 Nl/hr) was passed over this catalyst. Catalyst: Zeolyst beta zeolite CP 7146; temperature of the catalyst bed: 255° C.;

LHSV: 0.26; WHSV: 0.5; water content: 0.14% w/w; mol ratio MeOH/Valerolactone: 3:1.

Over a period of 287 hours, at time intervals as indicated in Table 1, samples were drawn and the following parameters were determined: (i) the amounts of methanol, valerolactone, M-2P, M-3P, M-4P and DME (by GC); (ii) the conversion (%) and selectivity towards formation of MP based on the initial amount of γ-valerolactone; (iii) the formation of DME based on the initial amount of methanol; (iv) the yield of MP relative to the amount of VL; (v) the mass balance based on:
total matter ("total")
VL+MP (i.e. M-2P+M-3P+M-4P)
VL+MP (i.e. M-2P+M-3P+M-4P)+PA
Results are presented in Table 1.

Example 2

The reaction of Example 1 was continued until 455 hours under conditions as described under Example 1, except that the temperature was raised to 275° C. Samples were withdrawn at time intervals as indicated in Table 2, and the same parameters were determined as in Example 1. Results are presented in Table 2

Example 3

The reaction of Example 1 was continued under conditions as described under Example 2 until 476 hours, except that the flow of $N_2$ was increased to 10 Nl/hr. Samples were withdrawn at time intervals as indicated in Table 3, and the same parameters were determined as in Example 1. Results are presented in Table 3.

Example 4

The reaction of Example 1 was continued until 501 hours under conditions as described under Example 3, except that 400 ppm methanesulphonic acid relative to the amount of VL was added to the reaction mixture and the flow of $N_2$ was decreased again to 5 Nl/hr. Samples were withdrawn at time intervals as indicated in Table 4, and the same parameters were determined as in Example 1. Results are presented in Table 4.

Example 5

The reaction of Example 1 was continued until 639 hours under conditions as described under Example 4, except that the temperature was decreased to 255° C. Samples were withdrawn at time intervals as indicated in Table 5, and the same parameters were determined as in Example 1. Results are presented in Table 5.

Example 6

The same reactor as described in example 1 was filled with 50 ml of silica-alumina catalyst 1D (Albemarle). A gaseous mixture of methanol, γ-valerolacone and N2 (5 Nl/hr) was passed over this catalyst. Temperature of the catalyst bed: 255° C.; LHSV of γ-valerolactone: 0.25; WHSV of γ-valerolactone: 0.6; water content: 0.25% w/w; mol ratio MeOH/valerolactone: 3.1:1. Over a period of 98.6 hours, at time intervals as indicated in Table 6, samples were drawn and the following parameters were determined: (i) the amounts of methanol, valerolactone, M-2P, M-3P, M-4P and DME (By GC); (ii) the conversion (%) and selectivity towards formation of MP based on the initial amount of γ-valerolactone; (iii) the formation of DME based on the initial amount of methanol; (iv) the yield of MP relative to the amount of VL Example 7

The reaction of example 6 was continued until 288.5 hours under conditions as described under example 5, except that the temperature was raised to 275° C. Samples were withdrawn at time intervals as indicated in Table 7.

Example 8

The reaction of example 7 was continued until 472.8 hours under conditions as described under example 7, except that 400 ppm methanesulphonic acid relative to the amount of VL was added to the reaction mixture. Samples were withdrawn at time intervals as indicated in Table 8

Example 9

The same reactor as described in example 1 was filled with 50 ml of silica-alumina catalyst 3D (Albemarle). A gaseous mixture of methanol, γ-valerolactone and N2 (5 Nl/hr) was passed over this catalyst. Temperature of the catalyst bed: 255° C.; LHSV of γ-valerolactone: 0.25; WHSV of γ-valerolactone: 0.6; water content: 0.11% w/w; mol ratio MeOH/valerolactone: 3:1. Over a period of about 500 hours, at time intervals as indicated in Table 9, samples were drawn and the following parameters were determined: (i) the amounts of methanol, valerolactone, M-2P, M-3P, M-4P and DME (By GC); (ii) the conversion (%) and selectivity towards formation of MP based on the initial amount of γ-valerolactone; (iii) the formation of DME based on the initial amount of methanol; (iv) the yield of MP relative to the amount of VL Example 10

Example 9 was repeated but now, after about 137 hours of reaction, 400 ppm p-toluensulphonic acid relative to the amount of VL was added to the reaction mixture. Samples were withdrawn as indicated in Table 10.

TABLE 1

| Entry | Duration of reaction (hrs) (cumulative) | Conversion (%) Valero lactone | MeOH | Selectivity (%) M-2P | M-3P | M-4P | total MP | g DME/ kg MP | Yield pentenoate relative to VL (%) Total | M-3P + M-4P | Mass balance out/in (mol %) total (%) | VL + MP | VL + MP + PA |
|---|---|---|---|---|---|---|---|---|---|---|---|---|---|
| 1 | 5 | 70 | 31 | 10 | 61 | 23 | 94 | 84 | 66 | 58 | 96 | 96 | 98 |
| 2 | 22 | 69 | 31 | 8.6 | 58 | 23 | 90 | 106 | 62 | 56 | 93 | 93 | 95 |
| 3 | 28 | 70 | 30 | 9.3 | 51 | 22 | 82 | 83 | 65 | 58 | 94 | 94 | 96 |

TABLE 1-continued

| | | | | | | | | | Yield pentenoate relative to VL (%) | | Mass balance out/in (mol %) | |
|---|---|---|---|---|---|---|---|---|---|---|---|---|
| | Duration of | Conversion (%) | | Selectivity (%) | | | | | | M-3P | VL | VL + |
| Entry | reaction (hrs) (cumulative) | Valero lactone | MeOH | M-2P | M-3P | M-4P | total MP | g DME/ kg MP | Total | + M-4P | total (%) | + MP | MP + PA |
| 4 | 54 | 66 | 26 | 8.5 | 61 | 25 | 95 | 48 | 63 | 57 | 97 | 97 | 98 |
| 5 | 76 | 68 | 31 | 7.3 | 54 | 23 | 84 | 132 | 57 | 53 | 90 | 89 | 91 |
| 6 | 100 | 66 | 34 | 5.8 | 47 | 22 | 75 | 226 | 50 | 46 | 85 | 84 | 85 |
| 7 | 117 | 54 | 23 | 6.5 | 57 | 31 | 94 | 73 | 51 | 48 | 97 | 97 | 98 |
| 8 | 124 | 54 | 22 | 6.1 | 56 | 31 | 93 | 65 | 50 | 47 | 98 | 96 | 98 |
| 9 | 140 | 53 | 22 | 6.0 | 55 | 31 | 92 | 71 | 49 | 46 | 98 | 96 | 98 |
| 10 | 148 | 52 | 22 | 6.0 | 56 | 32 | 94 | 77 | 49 | 46 | 98 | 97 | 99 |
| 11 | 170 | 52 | 21 | 5.8 | 54 | 32 | 92 | 72 | 47 | 44 | 98 | 96 | 98 |
| 12 | 220 | 49 | 20 | 5.4 | 54 | 33 | 93 | 64 | 45 | 43 | 99 | 96 | 98 |
| 13 | 245 | 46 | 19 | 5.4 | 54 | 34 | 93 | 67 | 43 | 41 | 98 | 97 | 99 |
| 14 | 267 | 45 | 19 | 5.3 | 53 | 35 | 93 | 78 | 41 | 39 | 98 | 97 | 99 |
| 15 | 287 | 44 | 19 | 5.3 | 51 | 34 | 90 | 85 | 40 | 38 | 98 | 96 | 98 |

TABLE 2

| | | | | | | | | | Yield pentenoate relative to VL (%) | | Mass balance out/in (mol %) | |
|---|---|---|---|---|---|---|---|---|---|---|---|---|
| | Duration of | Conversion (%) | | Selectivity (%) | | | | | | M-3P | VL | VL + |
| Entry | reaction (hrs) (cumulative) | Valero lactone | MeOH | M-2P | M-3P | M-4P | total MP | g DME/ kg MP | Total | + M-4P | total (%) | + MP | MP + PA |
| 16 | 290 | 79 | 28 | 12.4 | 55 | 17 | 85 | 59 | 67 | 57 | 93 | 88 | 90 |
| 17 | 231 | 78 | 29 | 11.8 | 55 | 18 | 84 | 71 | 65 | 56 | 92 | 88 | 89 |
| 18 | 333 | 75 | 26 | 11.1 | 54 | 19 | 85 | 48 | 63 | 55 | 94 | 89 | 90 |
| 19 | 360 | 71 | 22 | 10.2 | 53 | 21 | 85 | 20 | 60 | 53 | 95 | 89 | 91 |
| 20 | 386 | 70 | 22 | 9.7 | 51 | 22 | 83 | 29 | 58 | 51 | 95 | 88 | 90 |
| 21 | 409 | 66 | 21 | 9.7 | 51 | 23 | 84 | 28 | 55 | 49 | 95 | 89 | 91 |
| 22 | 432 | 64 | 20 | 9.3 | 51 | 23 | 83 | 27 | 53 | 47 | 95 | 89 | 91 |
| 23 | 455 | 62 | 19 | 9.2 | 50 | 24 | 83 | 28 | 52 | 46 | 95 | 90 | 92 |

TABLE 3

| | | | | | | | | | Yield pentenoate relative to VL (%) | | Mass balance out/in (mol %) | |
|---|---|---|---|---|---|---|---|---|---|---|---|---|
| | Duration of | Conversion (%) | | Selectivity (%) | | | | | | M-3P | VL | VL + |
| Entry | reaction (hrs) (cumulative) | Valero lactone | MeOH | M-2P | M-3P | M-4P | total MP | g DME/ kg MP | Total | + M-4P | total (%) | + MP | MP + PA |
| 24 | 456 | 57 | 18 | 9.3 | 48 | 24 | 81 | 43 | 46 | 41 | 94 | 89 | 91 |
| 25 | 472 | 57 | 18 | 9.0 | 47 | 24 | 79 | 39 | 45 | 40 | 94 | 88 | 91 |
| 26 | 476 | 56 | 19 | 9.1 | 47 | 24 | 80 | 54 | 45 | 39 | 94 | 89 | 91 |

TABLE 4

| | | | | | | | | | Yield pentenoate relative to VL (%) | | Mass balance out/in (mol %) | |
|---|---|---|---|---|---|---|---|---|---|---|---|---|
| | Duration of | Conversion (%) | | Selectivity (%) | | | | | | M-3P | VL | VL + |
| Entry | reaction (hrs) (cumulative) | Valero lactone | MeOH | M-2P | M-3P | M-4P | total MP | g DME/ kg MP | Total | + M-4P | total (%) | + MP | MP + PA |
| 27 | 478 | 62 | 19 | 9.5 | 51 | 24 | 85 | 15 | 53 | 47 | 96 | 91 | 93 |
| 28 | 496 | 81 | 29 | 13.5 | 56 | 16 | 85 | 58 | 69 | 58 | 93 | 88 | 90 |
| 29 | 501 | 89 | 39 | 16.5 | 49 | 11 | 77 | 155 | 68 | 54 | 84 | 79 | 80 |

TABLE 5

| Entry | Duration of reaction (hrs) (cumulative) | Conversion (%) Valero lactone | MeOH | Selectivity (%) M-2P | M-3P | M-4P | total MP | g DME/ kg MP | Yield pentenoate relative to VL (%) Total | M-3P + M-4P | Mass balance out/in (mol %) total (%) | VL + MP | VL + MP + PA |
|---|---|---|---|---|---|---|---|---|---|---|---|---|---|
| 30 | 518 | 73 | 30 | 7.4 | 69 | 20 | 96 | 65 | 70 | 64 | 96 | 97 | 98 |
| 31 | 524 | 73 | 31 | 8.7 | 70 | 18 | 97 | 70 | 71 | 65 | 97 | 97 | 99 |
| 32 | 546 | 74 | 30 | 8.8 | 71 | 18 | 97 | 58 | 72 | 65 | 98 | 98 | 99 |
| 33 | 572 | 76 | 34 | 8.2 | 69 | 17 | 94 | 86 | 71 | 65 | 95 | 96 | 97 |
| 34 | 594 | 76 | 36 | 7.7 | 67 | 17 | 92 | 117 | 70 | 64 | 92 | 94 | 95 |
| 35 | 613 | 75 | 35 | 7.4 | 69 | 17 | 93 | 104 | 70 | 64 | 94 | 95 | 96 |
| 36 | 639 | 74 | 34 | 7.1 | 69 | 18 | 93 | 100 | 69 | 64 | 94 | 95 | 97 |

TABLE 6

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 37 | 4.0 | 64 | 57 | 28 | 41 | 22.1 | 91 | 410 | 58 | 40 |
| 38 | 29.0 | 58 | 44 | 25 | 43 | 29.1 | 97 | 290 | 56 | 41 |
| 39 | 53.3 | 53 | 41 | 23 | 41 | 33.3 | 98 | 300 | 51 | 39 |
| 40 | 77.3 | 51 | 42 | 21 | 39 | 34 | 93 | 350 | 48 | 37 |
| 41 | 98.6 | 49 | 40 | 21 | 40 | 36 | 97 | 334 | 47 | 37 |

TABLE 7

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 42 | 115.2 | 62 | 50 | 27 | 42 | 26 | 96 | 329 | 59 | 43 |
| 43 | 121.2 | 61 | 52 | 25 | 40 | 26 | 91 | 393 | 55 | 40 |
| 44 | 138.7 | 60 | 49 | 26 | 41 | 29 | 96 | 337 | 57 | 42 |
| 45 | 144.5 | 60 | 50 | 25 | 40 | 28 | 92 | 370 | 55 | 40 |
| 46 | 163.4 | 58 | 46 | 26 | 41 | 31 | 98 | 310 | 57 | 42 |
| 47 | 168.2 | 57 | 49 | 25 | 41 | 31 | 97 | 350 | 55 | 41 |
| 48 | 194.4 | 58 | 47 | 24 | 39 | 30 | 93 | 341 | 54 | 40 |
| 49 | 218.4 | 57 | 47 | 24 | 39 | 31 | 94 | 350 | 54 | 40 |
| 50 | 238.9 | 59 | 50 | 23 | 37 | 29 | 89 | 397 | 52 | 39 |
| 51 | 258.7 | 55 | 46 | 23 | 39 | 33 | 95 | 345 | 53 | 40 |
| 52 | 282.7 | 53 | 44 | 24 | 40 | 35 | 98 | 330 | 52 | 40 |
| 53 | 288.5 | 53 | 46 | 23 | 39 | 34 | 97 | 358 | 51 | 39 |

TABLE 8

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 54 | 304.8 | 53 | 41 | 22 | 39 | 35 | 95 | 300 | 50 | 39 |
| 55 | 309.6 | 52 | 39 | 22 | 40 | 36 | 98 | 275 | 51 | 39 |
| 56 | 331.2 | 53 | 33 | 21 | 40 | 35 | 97 | 200 | 51 | 40 |
| 57 | 360.0 | 55 | 39 | 20 | 40 | 33 | 92 | 271 | 50 | 39 |
| 58 | 384.0 | 55 | 37 | 20 | 42 | 34 | 95 | 236 | 52 | 41 |
| 59 | 403.2 | 54 | 37 | 21 | 43 | 34 | 98 | 225 | 53 | 42 |
| 60 | 427.2 | 54 | 36 | 20 | 42 | 34 | 96 | 225 | 52 | 41 |

TABLE 8-continued

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 61 | 448.8 | 54 | 36 | 20 | 42 | 34 | 96 | 226 | 52 | 41 |
| 62 | 472.8 | 56 | 35 | 20 | 41 | 33 | 94 | 207 | 52 | 42 |

TABLE 9

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 63 | 4.8 | 77 | 59 | 30 | 54 | 11 | 95 | 276 | 75 | 52 |
| 64 | 31.2 | 78 | 51 | 25 | 56 | 13 | 94 | 210 | 75 | 55 |
| 65 | 50.4 | 77 | 47 | 22 | 58 | 15 | 95 | 182 | 75 | 58 |
| 66 | 76.8 | 76 | 45 | 20 | 58 | 16 | 94 | 171 | 73 | 58 |
| 67 | 103.2 | 75 | 44 | 19 | 59 | 18 | 96 | 157 | 74 | 59 |
| 68 | 146.4 | 72 | 47 | 17 | 59 | 19 | 95 | 210 | 70 | 58 |
| 69 | 172.8 | 71 | 42 | 17 | 61 | 21 | 99 | 147 | 72 | 60 |
| 70 | 194.4 | 71 | 41 | 16 | 60 | 21 | 97 | 145 | 71 | 59 |
| 71 | 223.2 | 71 | 36 | 16 | 60 | 22 | 98 | 108 | 69 | 58 |
| 72 | 247.2 | 71 | 38 | 15 | 58 | 22 | 95 | 135 | 67 | 57 |
| 73 | 271.2 | 70 | 37 | 15 | 59 | 23 | 97 | 128 | 67 | 57 |
| 74 | 295.2 | 69 | 37 | 14 | 59 | 23 | 97 | 129 | 66 | 57 |
| 75 | 314.4 | 69 | 38 | 14 | 58 | 23 | 95 | 139 | 66 | 56 |
| 76 | 340.8 | 68 | 37 | 14 | 58 | 24 | 96 | 135 | 65 | 56 |
| 77 | 362.4 | 68 | 37 | 14 | 58 | 24 | 96 | 133 | 65 | 56 |
| 78 | 384.0 | 67 | 35 | 14 | 59 | 25 | 98 | 109 | 66 | 57 |
| 79 | 410.4 | 67 | 35 | 13 | 59 | 25 | 98 | 117 | 65 | 56 |
| 80 | 439.2 | 67 | 35 | 13 | 57 | 25 | 95 | 122 | 64 | 55 |
| 81 | 463.2 | 66 | 35 | 13 | 58 | 26 | 96 | 124 | 64 | 55 |
| 82 | 487.2 | 66 | 36 | 13 | 57 | 26 | 95 | 143 | 63 | 54 |
| 83 | 506.4 | 64 | 36 | 13 | 59 | 26 | 98 | 138 | 63 | 55 |

TABLE 10

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 84 | 1.2 | 79 | 66 | 28 | 44 | 8 | 79 | 434 | 63 | 41 |
| 85 | 19.2 | 78 | 51 | 27 | 57 | 12 | 95 | 220 | 74 | 54 |
| 86 | 21.6 | 78 | 48 | 24 | 58 | 13 | 95 | 196 | 74 | 55 |
| 87 | 24.0 | 78 | 48 | 23 | 59 | 14 | 96 | 185 | 74 | 56 |
| 88 | 48.0 | 77 | 46 | 22 | 59 | 15 | 95 | 187 | 74 | 57 |
| 89 | 72.0 | 75 | 43 | 20 | 61 | 17 | 99 | 144 | 74 | 59 |
| 90 | 91.2 | 74 | 42 | 19 | 62 | 18 | 99 | 144 | 74 | 59 |
| 91 | 93.6 | 74 | 42 | 18 | 61 | 18 | 97 | 150 | 72 | 58 |
| 92 | 96.0 | 75 | 43 | 18 | 59 | 18 | 94 | 160 | 71 | 57 |
| 93 | 112.8 | 74 | 42 | 18 | 60 | 19 | 96 | 154 | 71 | 58 |
| 94 | 117.6 | 74 | 43 | 17 | 58 | 18 | 93 | 177 | 69 | 57 |
| 95 | 122.4 | 74 | 43 | 17 | 59 | 19 | 94 | 167 | 70 | 57 |
| 96 | 136.8 | 73 | 42 | 17 | 61 | 19 | 97 | 152 | 71 | 58 |
| 97 | 141.6 | 74 | 43 | 16 | 59 | 19 | 94 | 178 | 69 | 57 |
| 98 | 158.4 | 74 | 42 | 16 | 59 | 19 | 93 | 167 | 69 | 58 |
| 99 | 160.8 | 75 | 42 | 15 | 60 | 18 | 93 | 167 | 69 | 58 |
| 100 | 163.2 | 75 | 43 | 15 | 60 | 18 | 93 | 172 | 69 | 58 |
| 101 | 180.0 | 74 | 44 | 14 | 61 | 18 | 93 | 178 | 69 | 59 |
| 102 | 187.2 | 74 | 43 | 13 | 62 | 18 | 93 | 173 | 69 | 60 |
| 103 | 189.6 | 74 | 44 | 13 | 62 | 18 | 93 | 184 | 69 | 60 |
| 104 | 213.6 | 75 | 45 | 12 | 63 | 18 | 93 | 187 | 69 | 60 |
| 105 | 237.6 | 74 | 47 | 11 | 65 | 18 | 94 | 200 | 70 | 62 |

TABLE 10-continued

| Entry | Duration of reaction (hrs) (cumulative) | Conversion (%) Valero lactone | MeOH | Selectivity (%) M-2P | M-3P | M-4P | Total MP | g DME/ kg MP | Yield pentenoate relative to VL (%) Total | M-3P + M-4P |
|---|---|---|---|---|---|---|---|---|---|---|
| 106 | 254.4 | 74 | 46 | 10 | 66 | 19 | 95 | 197 | 70 | 62 |
| 107 | 256.8 | 73 | 47 | 10 | 66 | 19 | 95 | 208 | 69 | 62 |
| 108 | 261.6 | 73 | 44 | 10 | 66 | 19 | 94 | 187 | 69 | 61 |
| 109 | 276.0 | 73 | 40 | 10 | 67 | 19 | 96 | 143 | 70 | 63 |

The invention claimed is:

1. Process for the preparation of pentenoic acid alkyl ester comprising:
   (a) contacting a 5-methylbutyrolactone with an alkanol and an acidic heterogeneous catalyst, wherein the process is carried out in the presence of between 20 ppm and 1000 ppm of a sulphonic acid relative to the amount of the 5-methylbutyrolactone, wherein the sulphonic acid has a pKa of 5 or less.

2. Process according to claim 1 wherein the acidic heterogeneous catalyst comprises a zeolite or an amorphous silica-alumina catalyst.

3. Process according to claim 1 wherein the acidic heterogeneous catalyst comprises a beta zeolite.

4. Process according to claim 1 wherein the sulphonic acid is methanesulphonic acid or p-toluenesulphonic acid.

5. Process according to claim 1 further comprising adding the sulphonic acid.

6. Process according to claim 1 wherein the process is carried out in the presence of from 0.26% to 10% wt water relative to the amount of the 5-methylbutyrolactone.

7. Process according to claim 1 wherein the alkanol is methanol, thereby forming pentenoic acid methyl ester.

8. Process according to claim 1 which is a continuous process.

9. Process according to claim 1 which is a repetitive batch process, wherein the process further comprises:
   (b) recovering the acidic heterogeneous catalyst from the pentenoic acid alkyl esters in the presence of said sulphonic acid having a pKa of 5 or less, wherein the amount of said sulphonic acid having a pKa of 5 or less in the recovered acidic heterogeneous catalyst is between 20 ppm and 1000 ppm relative to the amount of 5-methylbutyrolactone; and
   (c) repeating (a) wherein at least part of the acidic heterogeneous catalyst in (a) is the recovered acidic heterogeneous catalyst obtained in (b).

10. Process according to claim 1 wherein the 5-methylbutyrolactone is produced by converting levulinic acid to 5-methylbutyrolactone in a hydrogenation reaction.

11. Process according to claim 10 wherein the levulinic acid is prepared by converting a C6 carbohydrate to levulinic acid in an acid-catalysed reaction.

12. Process to produce adipic acid dimethyl ester comprising converting pentenoic acid methyl ester produced in the process according to claim 7 to adipic acid dimethyl ester in a carbonylation reaction in the presence of CO and methanol.

13. Process to produce adipic acid comprising converting adipic acid dimethyl ester produced in the process of claim 12 in a hydrolysis reaction.

* * * * *